United States Patent
Orange et al.

(10) Patent No.: US 7,168,332 B2
(45) Date of Patent: Jan. 30, 2007

(54) POWDER SAMPLING DEVICE

(75) Inventors: Christian Orange, Bricquebec (FR); Christian Trevisan, Livry Gargan (FR); Joel Tourre-Ledoux, Pujaut (FR)

(73) Assignee: Compagnie Generale des Matieres Nucleaires, Velizy-Villacoublay (FR)

( * ) Notice: Subject to any disclaimer, the term of this patent is extended or adjusted under 35 U.S.C. 154(b) by 0 days.

(21) Appl. No.: 10/541,337

(22) PCT Filed: May 13, 2004

(86) PCT No.: PCT/FR2004/050192

§ 371 (c)(1),
(2), (4) Date: Jul. 1, 2005

(87) PCT Pub. No.: WO2004/104556

PCT Pub. Date: Dec. 2, 2004

(65) Prior Publication Data
US 2006/0048587 A1  Mar. 9, 2006

(30) Foreign Application Priority Data
May 16, 2003  (FR)  ................................. 03 05878

(51) Int. Cl.
G01N 1/20 (2006.01)

(52) U.S. Cl. ................ 73/863.44; 73/863.41; 73/863.42; 73/863.54; 73/864.51

(58) Field of Classification Search .................. 73/863, 73/863.41–863.44, 863.51–863.55, 864, 73/864.51
See application file for complete search history.

(56) References Cited

U.S. PATENT DOCUMENTS

| | | | | |
|---|---|---|---|---|
| 2,668,447 A | * | 2/1954 | Lenhart | 73/863.51 |
| 3,091,969 A | * | 6/1963 | Romanchuk et al. | 73/863.31 |
| 3,253,470 A | * | 5/1966 | Platzer et al. | 73/863.55 |
| 3,735,641 A | * | 5/1973 | Bink et al. | 73/863.43 |
| 3,750,478 A | | 8/1973 | Keene | |
| 3,782,200 A | * | 1/1974 | Maas | 73/863.51 |
| 3,802,270 A | * | 4/1974 | Daniels et al. | 73/863.52 |
| 4,024,765 A | | 5/1977 | Abonnenc | |
| 4,026,154 A | | 5/1977 | Pfeiffer et al. | |
| 4,056,983 A | * | 11/1977 | Mazzetti | 73/863.44 |
| 4,574,645 A | * | 3/1986 | Allen et al. | 73/863.51 |
| 4,587,856 A | * | 5/1986 | Otis | 73/863.51 |
| 5,072,624 A | * | 12/1991 | Montgomery | 73/863.91 |
| 5,974,900 A | * | 11/1999 | Kalidindi | 73/863.57 |
| 6,520,035 B2 | * | 2/2003 | Long et al. | 73/864.32 |

FOREIGN PATENT DOCUMENTS

| | | |
|---|---|---|
| DE | 295 02 487.9 | 4/1995 |
| DE | 297 20 233 | 1/1998 |

* cited by examiner

Primary Examiner—Hezron Williams
Assistant Examiner—David A. Rogers
(74) Attorney, Agent, or Firm—Pearne & Gordon LLP

(57) ABSTRACT

The powder sampling device comprises, next to a vertical channel (1) a drawer that is also vertical which may be lowered so that a groove (5) passes into a sampling mouth (12). A flap (15) may be extended to direct the powder towards the groove (5) temporarily and fill it, without the drawer (4) or the flap (15) disrupting the flow in normal circumstances nor causing any residue of powder likely to alter the measurements. In particular, the flap (15), the groove (5) and the corbelled section (2) have faces (6, 8) that are heavily angled on which the powder can only slide.

3 Claims, 3 Drawing Sheets

POWDER SAMPLING DEVICE

BACKGROUND OF THE INVENTION

This invention relates to a powder sampling device.

It may be used in particular to take intermittent samples of powder flowing more or less continuously in an industrial process, in order to check the composition or quality, and is particularly advantageous if the volumes must be invariable, fine or are dangerous.

Traditional sampling devices include valves, taps or analogous devices, but they are poorly suited to powders, which can easily penetrate into moving parts and cause them to seize, and providing an efficient seal against leaks of dangerous materials is hard to ensure. Furthermore, it is difficult to adjust the volume that is sampled, with such means.

Another major problem that needs to be resolved to obtain satisfactory samples consist of avoiding stagnation of the powder from an earlier moment in the flow around the sampling device, which would be mixed in with the powder sampled and comprise the reliability of the measurement.

Another problem which could be important consists of avoiding the sampling device from disrupting the flow, which could furthermore lead to the problem mentioned above, of creating a pocket of stagnant powder in front of the device.

The powder sampling device of the document U.S. Pat. No. 4,024,765 comprises: an appended part, generally empty of powders, of a powder flow channel; a reciprocating member traversing a wall of the appended part, and sliding between a first position where a groove in it extends into the appended part and a second position where the groove extends beyond the appended part, the groove being limited by faces where the powder slides or falls; and a flap in the flow channel, moving between a withdrawn position where it has no essential effect on the flow of the powders and an extended position where it directs the flow of the powders into the appended part.

It appears that the flow of the powders passes beside the sampling device in normal conditions, and is not likely to be disrupted by it or to foul it by stagnating powder. In the sampling position, the powder or a portion of it is on the contrary temporarily directed towards the appended part containing the sampling device and fills the reciprocating member groove, which may then be moved to the second position where the volume of the powder contained in the groove is sampled and analysed. In this patent, the reciprocating member is pushed into the appended part when the powder fills it. A powder sample enters the groove, then the reciprocating member is removed and is turned over. The content of the groove then escapes from it entirely. This design may be criticized in that the reciprocating member is moved in a translation and rotation movement, which is complicated, increases the possibility of friction and seizure, and that quite a large volume of powder must fill the appended part for a sample to be taken.

A representative sample of the flow at a specific given time may become impossible.

BRIEF SUMMARY OF THE INVENTION

The invention may be considered as a perfection of this design: it is original in that the reciprocating member has an upright orientation (more or less vertical) and that the groove is limited by a ceiling face and an angled face which extend a base plate of the appended part when the reciprocating member is in the first position.

In a preferred embodiment, the appended part is a lateral extension of the channel and its base plate is angled towards the channel; the second position is situated below the first position; and the flap rotates, the withdrawn position being more or less vertical and the extended position being angled through the channel, the flap touching the base plate just below the groove in the first position of the drawer.

It is guaranteed that the volume of powder directed towards the appended part, but not being part of the sample taken, rejoins the main flow by sliding on the angled base plate; the continuity of this angled base plate and the angled face of the groove ensures that it is filled, by means of the regularity of the flow; and the proximity of the groove and the end of the flap in the extended position ensures that the groove is filled even with a low powder flow rate. Furthermore, a simple translation movement is sufficient to impose the flow of the powder out of the groove when in the withdrawn position; and if it is intended to stop sampling, the flap is simply folded back and the contents of the groove return to the main flow.

Even more satisfactory operating and sampling conditions are achieved if the flap is a spout comprising an incurved wall extending into a second lateral extension of the channel, as the flap in no way disrupts the flow in the withdrawn position, but it ensures the powder is gathered towards the groove in the extended position.

BRIEF DESCRIPTION OF THE SEVERAL VIEWS OF THE DRAWING

The invention will now be described by means of FIGS. 1 to 3, which represent the three main states of the device.

DETAILED DESCRIPTION OF THE INVENTION

Figure 1:
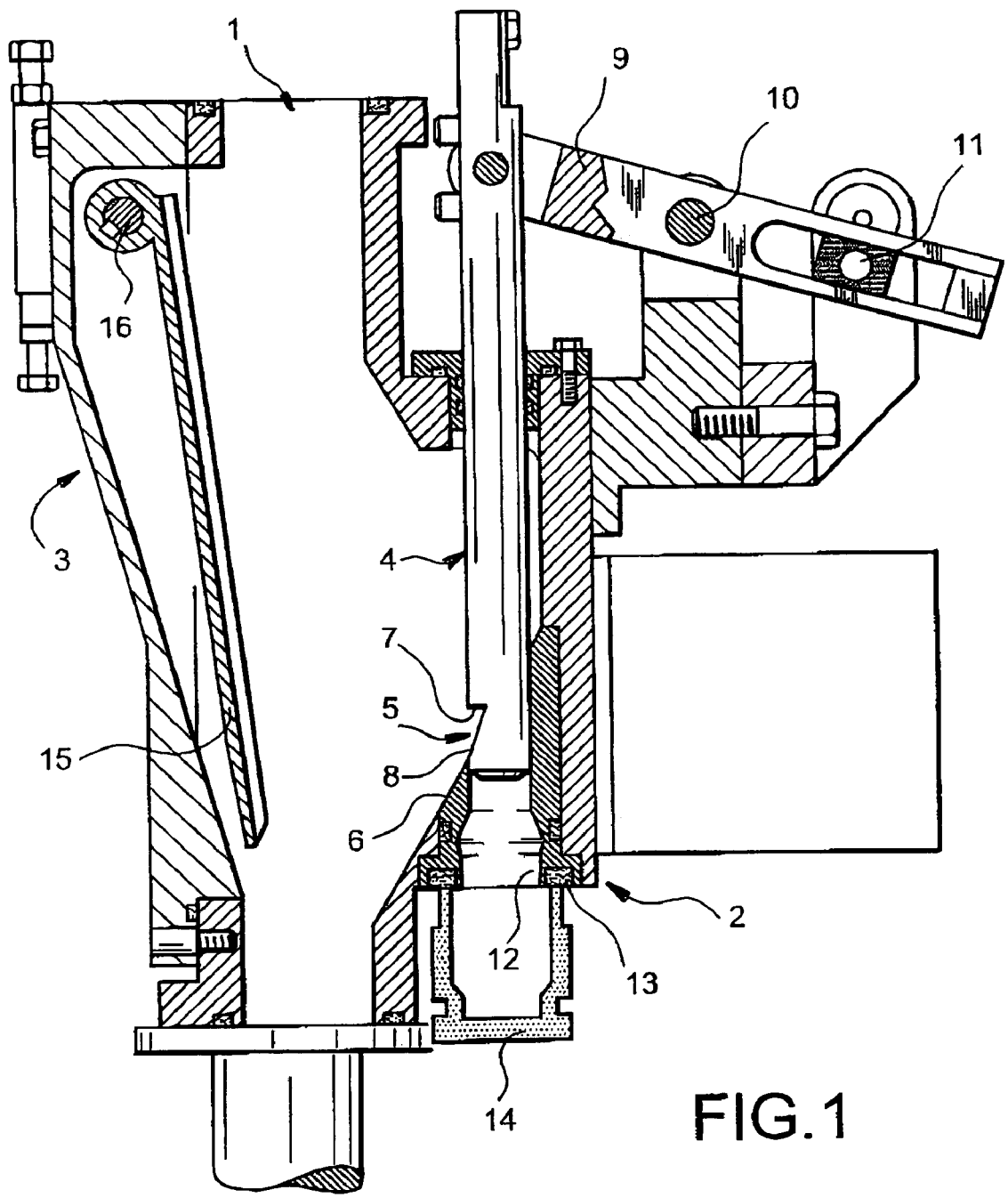
FIG. 1 shows a powder sampling device according to an embodiment of the invention in a state in which powder flows freely.

In FIG. 1, the powder flows freely. It falls via a vertical channel 1, whose sampling section comprises however an appended part composed of two lateral extensions 2 and 3, situated opposite one another on the periphery. The first contains a reciprocating member 4 which traverses it from one side to the other and comprises a vertical rod featuring a groove 5. The groove 5 extends to just above an inside base plate 6 of the lateral extension 2 that is angled towards the channel 1, and it is limited by a ceiling face 7 and above all by an angled face 8 which, in the position shown, extends the base plate 6. The reciprocating member 4 is articulated to a lever 9 above the lateral extension 2, and the lever 9 tilts around a pivot 10, and is driven on the opposite side by an eccentric shaft 11 driven by a motor that is not shown. Below the lateral extension 2 extends a mouth section 12 that the reciprocating member 4 may occupy partially that is surrounded by a flat seal 13 under which a beaker 14 may be positioned to collect the samples.

The lateral extension 3 comprises a flap 15 in the form of a spout, presenting incurved sections dished in the middle which run more or less vertically in the configuration shown in FIG. 1, where it is withdrawn: it therefore does not essentially disrupt the flow of the powder through the channel 1. It is attached to an upper rotation shaft 16 driven by another motor, which is not shown either.

Figure 2:
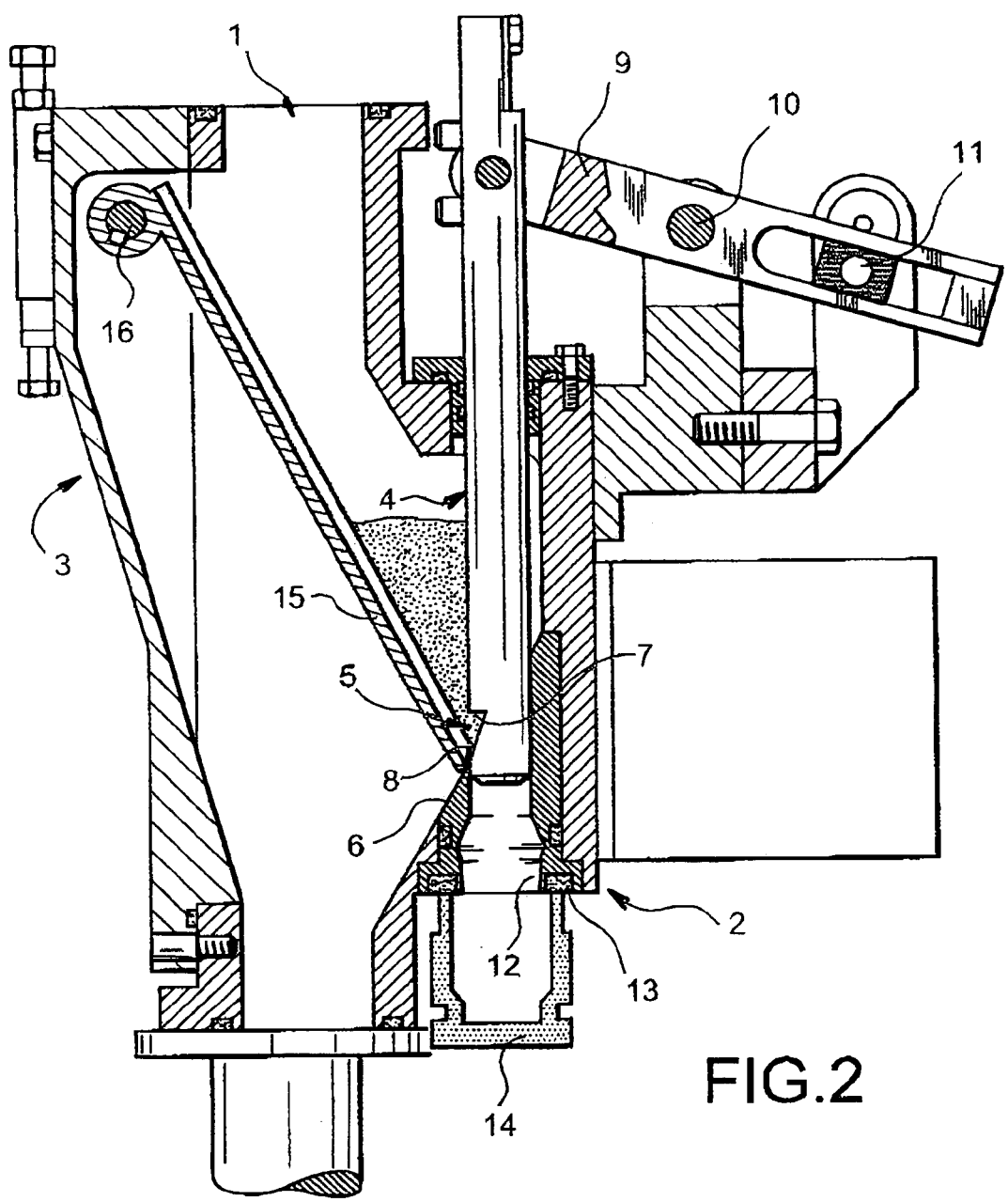
FIG. 2 shows the powder sampling device of FIG. 1 during a sampling operation in a state in which powder fills a groove.
Figure 3:
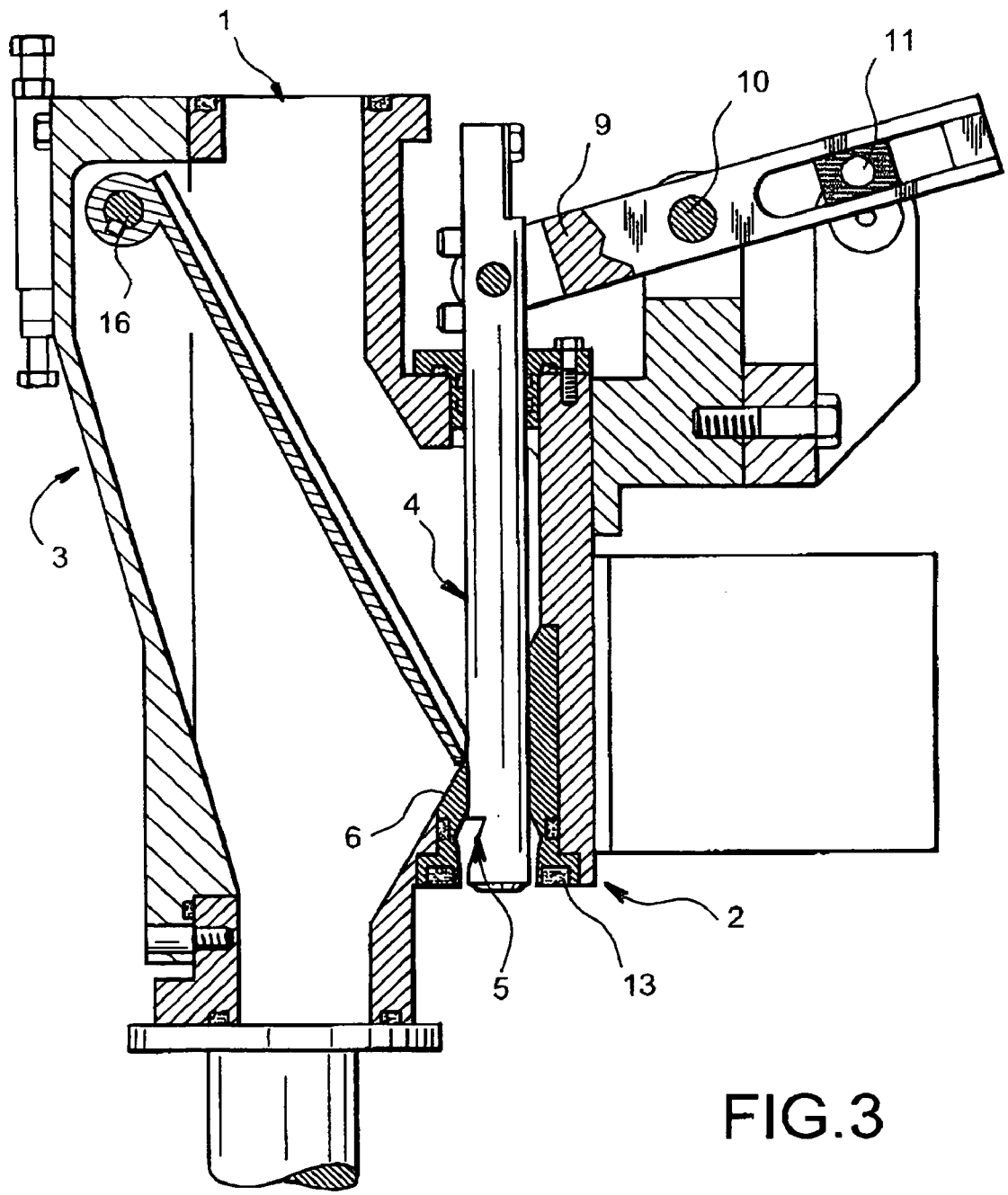
FIG. 3 shows the power sampling device of FIG. 1 in a state in which powder can be discharged from the groove.

We begin by referring to FIGS. 2 and 3 to discover how the powder sample is made. The flap 15 is firstly extended by rotation of the upper rotation shaft 16 to a state where it extends through the channel 1 and its end touches the base plate 6 of the lateral extension 2, just below the groove 5 in the raised position shown in FIG. 2. At least a portion of the powder flow is directed towards the appended section of the channel 1 formed by the inside of the lateral extension 2, and in particular in the volume of the groove 5 which is completely filled. It should be noted that if the flap 15 has incurved walls, it can make the powder that it intercepts converge into a narrower flow which consequently fills the groove 5 more easily, especially if its section becomes narrower towards the bottom, which makes the device advantageous even with low powder flow rates, as it can even be envisaged to direct almost all of the powder flow temporarily towards the groove 5. When the groove is filled, as shown in FIG. 2, tilting the lever 9 lowers the reciprocating member 4 and places the groove 5 in the mouth section 12 as shown in FIG. 3, and its contents run into the beaker 14 or other container. The slope of the angled face 8 is sufficient for the powder to flow with no retention, and the powder even flows completely from the base plate 6 of the lateral extension 2 as soon as the flap 15 is removed and returns to its initial position of FIG. 1; as this position is more or less vertical, there is no residue of the powder on the flap 15 either. The sample taken will therefore be completely representative of the powder flow at that time. Similarly, the powder which may have accumulated under the ceiling face 7 is completely detached when the sample flows from the groove 5; the ceiling face 7 is therefore called a powder chute face, and the angled face 8 is called a powder slide face (as the base plate 6).

The invention claimed is:

1. Powder sampling device comprising:

a lateral extension, generally empty of powders, coupled to a powder flow channel (1) and having an angled base plate;

a reciprocating member (4) having a groove traversing a wall of the lateral extension and sliding between a first position wherein said groove is located within the lateral extension in order to collect a powder sample and a second position wherein the groove is located outside the lateral extension in order to release the collected powder sample, the groove being defined by a ceiling face (7) and an angled face (8); and a flap (15) in the flow channel that moves between a withdrawn position where it has essentially no effect on the flow of the powders and an extended position where it directs the flow of the powders into the groove, wherein the reciprocating member (4) has an upright orientation and that the angled face is parallel to and extends from the base plate of the lateral extension when the reciprocating member is in the first position.

2. Powder sampling device of claim 1, wherein:

the base plate (6) is angled towards the channel;

the second position is situated below the first position; and the flap movement rotates from an essentially vertical, withdrawn position to an angled, extended position through the channel, the extended position allowing the flap to touch the base plate just below the groove when the reciprocating member is in the first position.

3. Powder sampling device of claim 2, wherein the flap is a spout having an incurved section.

* * * * *